United States Patent [19]
Wijnman et al.

[11] Patent Number: 5,726,303
[45] Date of Patent: Mar. 10, 1998

[54] METHOD OF PREPARING LACITOL MONOHYDRATE AND DIHYDRATE

[75] Inventors: Christiaan F. Wijnman, Woudrichem; John A. van Velthuijsen, Gorinchem; Hendrik van den Berg, Vuren, all of Netherlands

[73] Assignee: C.V. Chemie Combinatie Amsterdam C.C.A., Gorinchem, Netherlands

[21] Appl. No.: 770,777

[22] Filed: Oct. 4, 1991

Related U.S. Application Data

[63] Continuation of Ser. No. 496,133, Mar. 19, 1990, abandoned, which is a continuation of Ser. No. 597,816, Apr. 9, 1984, abandoned, which is a division of Ser. No. 321,726, Nov. 16, 1981, abandoned.

[51] Int. Cl.$^6$ ............................................ C07H 1/00
[52] U.S. Cl. ........................ 536/120; 536/1.1; 536/4.1
[58] Field of Search ..................... 536/1.1, 4.1, 127, 536/120

[56] References Cited

U.S. PATENT DOCUMENTS

| | | | |
|---|---|---|---|
| 3,957,976 | 5/1976 | Sugimoto | 514/23 |
| 4,117,173 | 9/1978 | Schiweck et al. | 536/4.1 |
| 4,408,041 | 10/1983 | Hirao et al. | 536/4.1 |
| 4,442,132 | 4/1984 | Kim | 426/549 |

FOREIGN PATENT DOCUMENTS

| | | | |
|---|---|---|---|
| 0039981 | 11/1981 | European Pat. Off. | 536/4.1 |

OTHER PUBLICATIONS

Mark van Bommel and Jan Kanters, "The Crystal and Molecular Structures of Lactitol Monohydrate and Lactitol Dihydrate", Nov. 13, 1979, a report presented to C.V. Chemie Combinatie Amsterdam C.C.A., presented at the 6th European Crystallographic Meeting, Barcelona, Spain on Jul. 28, 1980.

Wolfrom et al, *Journal of American Chemical Society* "Crystalline Lactositol", vol. 60, Mar. 1938, pp. 571–573.

Wolfrom et al, *Journal of American Chemical Society*, "Lactitol Dihydrate", vol. 74, Feb. 20, 1952, p. 1105.

van Velthuijsen, *J. of Agricultural and Food Chemistry*, "Food Add Der. from Lactose", vol. 27, Jul.–Aug. 1979, pp. 680–686.

van Bommel et al. A report Presented at the 6th European Crystall. Meeting, Barcelona Spain on Jul. 28, 1980.

*Primary Examiner*—Elli Peselev
*Attorney, Agent, or Firm*—Martin Smolowitz

[57] ABSTRACT

The invention relates to the new product lactitol monohydrate and to a method for the production of crystalline lactitol. The crystalline lactitol monohydrate can be obtained bij seeding an aqueous lactitol solution of a special concentration under special conditions causing the lactitol monohydrate to crystallize and recovering the product. From the mother liquor a further amount of lactitol dihydrate can be recovered. Crystalline lactitol dihydrate can be obtained using different special conditions. Lactitolmonohydrate can further be obtained by mixing one part bij weight of an aqueous lactitol solution of a suited concentration with 1 tot 3 parts bij weight of methanol or ethanol and cooling the mixture to 15° tot 25° C.

8 Claims, 2 Drawing Sheets

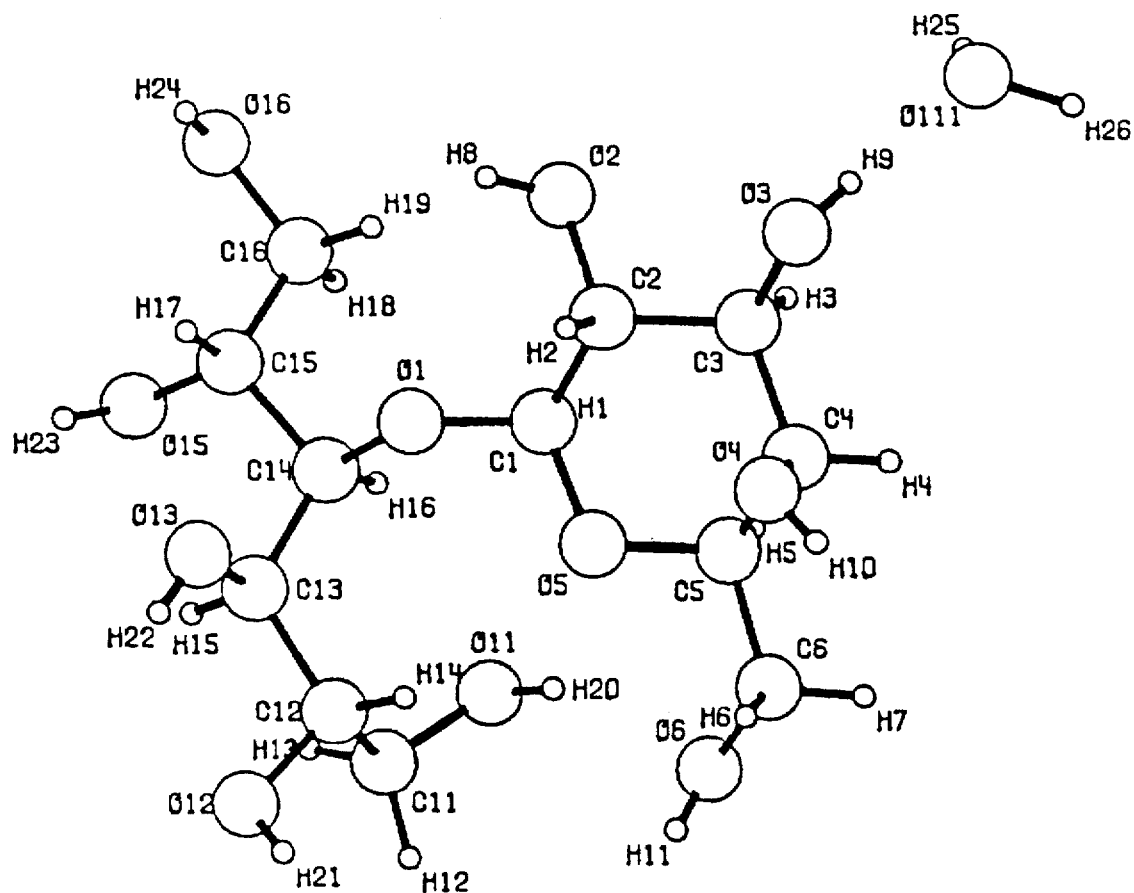
FIG_2

METHOD OF PREPARING LACTITOL MONOHYDRATE AND DIHYDRATE

This application is a continuation application of Ser. No. 07/496,133 filed Mar. 19, 1990 abn, which is a continuation application of Ser. No. 06/597,816 filed Apr. 9, 1984 abn, which is a divisional application of Ser. No. 06/321,726 filed Nov. 16, 1981, all now abandoned.

The invention relates to a method for the production of lactitol monohydrate and to a method for the production of crystalline lactitol by crystallization from an aqueous solution of lactitol.

Lactitol is lactose the glucose portion of which has been hydrogenated to sorbitol. Lactitol has the systematical name 4-β-D-galactopyranosyl-D-sorbitol.

The preparation of lactitol is of general knowledge. Like described in "Agricultural and Food Chemistry", July-August 1979, 27, 680-686 a 30-40 percent by weight lactose solution (based on the sum total) is normally used as the starting material such solution being hydrogenated at 100° C. and under a hydrogen pressure of 40 atmospheres in the presence of Raney-nickel. Upon the sedimentation of the catalyst the hydrogenated solution is filtrated and purified by means of ion-exchangers and activated carbon.

The relative sweetness of lactitol amounts to 36% when compared with the sweetness of a 5% saccharose solution. It thus is clearly less sweet than sorbitol (relative sweetness of 55%) and xylitol (relative sweetness of 96%) (vide "Agricultural and Food Chemistry", July-August 1979, 27, 680-686).

Like reported in a German Patent (Maizena, 1974) the hydrolysis of lactitol by α-glucosidase (maltase) is much slower than that of lactose and maltose.

Whereas lactose is hydrolyzed completely by β-galactosidase within 45 minutes lactitol is only hydrolyzed for 10-15% within the same period of time. Hence lactitol will only be decomposed to a minor degree in the alimentary track so that it is suitable as a replacement for sugar in products to be used by diabetics.

Lactitol is also suitable to be used in low-caloric foods.

Lactitol is less hygroscopic than sorbitol, glycerol and xylitol and may consequently be used in the preparation of certain bakery products for diabetics such as light biscuits (Dutch Patent Application 78.11204). Lactitol may therefore also be used in moisture insensitive coatings for chewing gum, gellies, fondant etc.

Furthermore lactitol possesses properties in view of which it is also well suited for several applications.

Due to the absence of a carbonyl group lactitol exibits a good stability against the exposure to heat and to alkali. Heating an aqueous solution of 10 percent by weight of lactitol adjusted to a pH-value of 13 with NaOH (1 hour at 100° C.) does not produce any discoloration whereas a lactose solution when heated under the same conditions shows a strong discoloration.

The stability of lactitol in acidic medium is comparable to that of lactose. After heating solutions of 10 percent by weight of lactitol adjusted to a pH-value of 1 and 2, respectively, with HCl (4 hours at 100° C.) it appeared that 5.1% and 1.4% respectively, of the lactitol was hydrolyzed. Lactose solutions appear to be hydrolyzed for 5.4% and 1.3%, respectively, when heated under the same conditions.

Heating at higher temperatures (170°-240° C.) caused anhydrisation of lactitol (production of lactitan).

Lactitol is soluble in water, dimethylsulfoxide and dimethylformamide and is miscible with other polyols (sorbitol, glycerol). It is slightly soluble in ethanol and diethylether.

Notwithstanding the fact that the literature (Saijonmaa, T., Heikonen, M., Linko, P., Milchwissenschaft 33 (1978) 733-736, Schiweck, H., Süsswaren 14 (1978) 13-21) considers lactitol to be a substance that may be crystallized very difficultly or not at all, nevertheless there are also reports to be found in the literature referring to a crystalline dihydrate (Wolfrom, M. L., Hann, Raymond M., Hudson, C. S., J. Am. Chem. Soc. 74 (1952) 1105) as well as to anhydric lactitol.

Crystalline anhydric lactitol is obtained by the repeated extraction of a concentrated aqueous lactitol solution with absolute ethanol (removal of water). The amorphous hydroscopic mass thus obtained was combined with absolute ethanol whereby lactitol.0 aq crystallized in a yield of 80% in a period of about one month.

Upon recrystallisation (dissolution in little water and additon of the same volume of ethanol) there were obtained small tetrahedral crystals having a melting point of 146° C. and a specific rotation of +14°. Heating these crystals at 140° C. under reduced pressure above $P_2O_5$ for a period of 54 hours did cause almost no loss of weight.

Lactitol dihydrate possesses a melting point of 76°-78° C. and has presumably first been described by Senderens, J. B., Compt.Rend. 170 (1920) 47-50. This investigator evaporated a hydrogenated lactose solution on a water bath until a syrupy mass was obtained, which mass kept at room temperature started to crystallize after some days; the product showed a melting point of 78° C. and a specific rotation of +12.2°.

Where drying the crystals at 130° C. to a constant weight caused a weight loss of 5% (water) Senderens thaught he had obtained the monohydrate.

It has now become apparent that when drying lactitol dihydrate at 130° C. for three days there will be a loss of weight of only 5%.

The publication by Senderen does not disclose any determination of the moisture content according to the Karl Fischer method; such a determination would presumebly have yielded a higher water content corresponding to the dihydrate (containing about 9.5 percent by weight of water).

Also in view of the low melting point (78° C.) it may thus be assumed that at that time Senderen has recovered the dihydrate instead of the monohydrate (the melting point indicated by him is 78° C., whereas lactitol monohydrate has a melting point of 121°-123° C. and the dihydrate has a melting point of 76°-78° C.).

Wolfrom, M. L., Hann, Raymond M., Hudson, C. S., (J. Am. Chem. Soc. 74 (1952) 1105) have also obtained the dihydrate and confirmed the composition there of on the basis of the elementary analysis. They found a melting point of 72.5°-74° C. and a specific rotation of +11.5°.

According to the invention there has now been found a crystalline lactitol monohydrate as well as a method for the production of crystalline lactitol by crystallization from an aqueous solution of lactitol, in which water is the sole solvent, by means of which lactitol monohydrate as well as lactitol dihydrate may be produced on an industrial scale, said method being characterized by a) seeding an aqueous solution of from 70 to 85 percent by weight, preferably from 78 to 82 percent by weight, of lactitol with lactitol monohydrate at from 45° C. to 55° C. and causing lactitol monohydrate to crystallize at from 40° C. to 50° C., preferably between 43° C. and 47° C., said lactitol monohydrate optionally being recovered, b) optionally subsequently cooling the mother liquor to from 15° C. to 25° C., preferably to from 18° C. to 22° C., seeding the same with crystalline lactitol monohydrate seeds and causing the lactitol monohydrate to crystallize at this temperature, said lactitol monohydrate optionally being recovered, c) optionally causing the mother liquor obtained under b) to crystallize further at from 10° C. to 25° C., preferably at from 15° C. to 20° C. and recovering lactitol dihydrate, or d) seeding an aqueous solution of from 57 to 76 percent by weight, preferably of from 68 to 76 percent by weight, in particular of from 72 to 74 percent by weight, of lactitol with crystalline lactitol dihydrate seeds and causing lactitol dihydrate to crystallize and recovering the same.

BRIEF DESCRIPTION OF THE DRAWINGS

FIG. 2 represents the molecular structure of lactitol monohydrate.

DETAILED DESCRIPTION OF THE INVENTION

Figure 1:
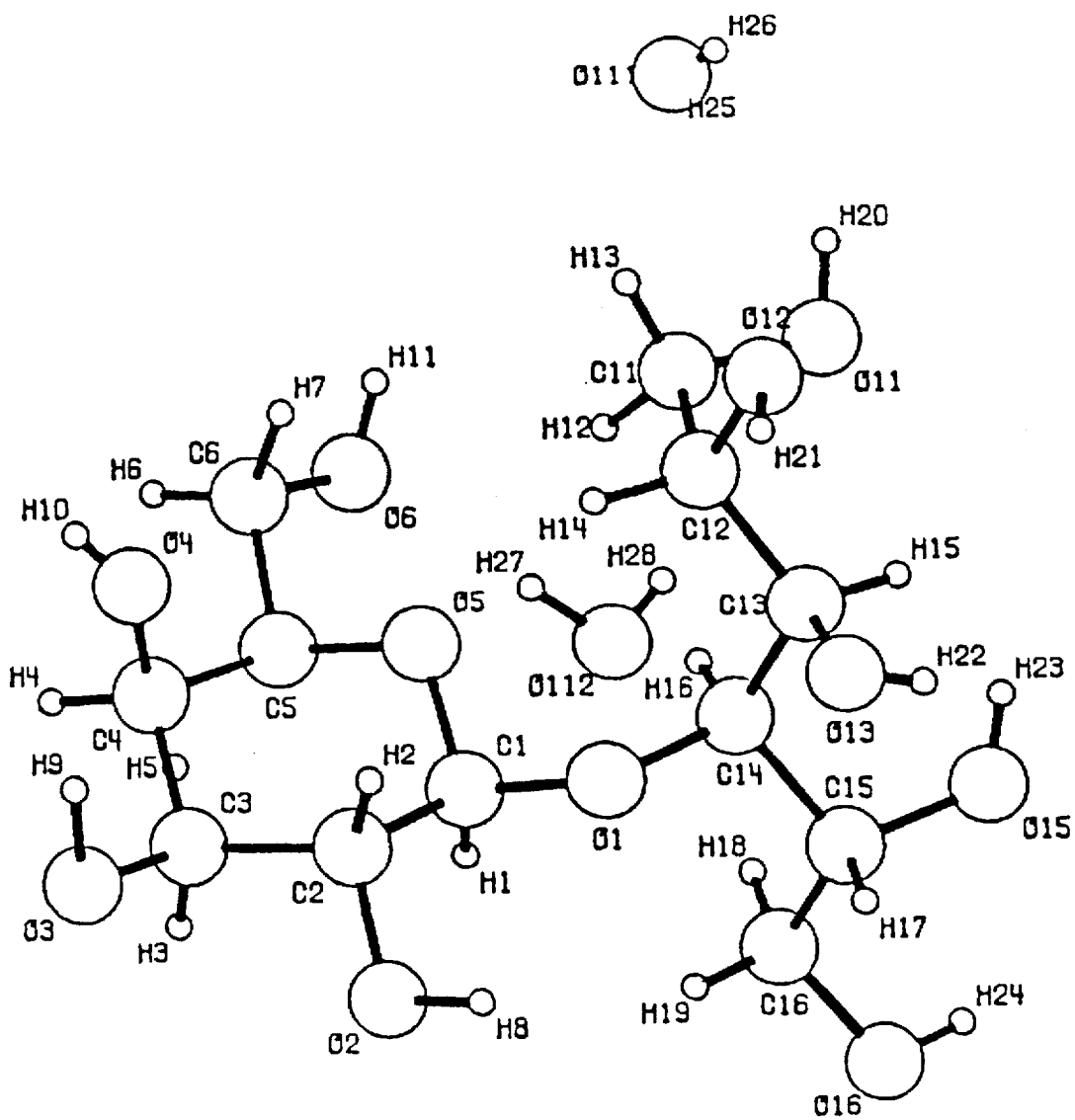
FIG. 1 represents the molecular structure of lactitol dihydrate.

The aqueous solution of lactitol may be prepared in an appropriate way by the hydrogenation of a lactose solution. By way of example there may be provided a solution of 1500 kg lactose dissolved in 2200 liter demineralized water at 60° C. The solution is heated to 100° C. and pressurized with hydrogen to a hydrogen pressure of 40 atmospheres to which there is added 100 kg Raney-nickel as a catalyst. Upon completion of the hydrogenation the solution thus obtained is passed over ion exchangers for the removal of nickel ions and organic acids formed thereby. After completing this treatment the solution shows a pH-value of 7.5 and a conductivity of 1.3 micro siemens (at 20°–25° C.) and a refractometer determined density of 30° Brix.

The measurement was carried out by means of a refractometer provided with a so-called sugar or Brix scale. This graduation is based on the percentage by weight of saccharose in a solution. For other sugars the same scale is used is an indication for the concentration (vide also Kirk-Othmer Encyclopedia of Chemical Technology, 2nd edition Vol. 19 pages 158 and 159).

From this purified lactitol solution there may be recovered also crystalline lactitol dihydrate upon concentrating said solution provided the crystallization is performed at 10°–37° C. and the solution is first seeded with crystalline lactitol dihydrate seeds. The dihydrate may also be obtained from the concentrated solution without seeding in course of time (vide example I). The crystallization may then be induced by a method known per se, such as scraping the walls of the crystallization vessel.

Lactitol monohydrate may be prepared very advantageously by seeding an aqueous solution of from 75 to 85 percent by weight of lactitol with lactitol monohydrate at 45°–55° C. and then causing the solution to crystallize at 40°–50° C. Thereby the lactitol monohydrate may be recovered in a crystallization yield of 40–60%. It is of particular advantage to seed the resulting mother liquor at 15°–25° C. with lactitol monohydrate and to cause the same to crystallize at this temperature. Thereby a crystallization yield of yet 20–25% is obtained.

Furthermore lactitol monohydrate may be produced by mixing 1 part by weight of an aqueous lactitol solution having a concentration of from 60 to 75 percent by weight with from 1 to 3 parts by weight of methanol or ethanol and subsequently cooling the mixture to 15°–25° C. while agitating. Thereby lactitol monohydrate crystallizes. It is of advantage therein to use 1 part by weight of a lactitol solution having a concentration of from 65–70 percent by weight and to mix the same with from 1 to 2 parts by weight of methanol or ethanol. In particular one will use 1 part by weight of the lactitol solution and will mix the same with 1 part by weight of ethanol whereupon one will allow the solution to cool to 18°–22° C. while agitating and then recover the crystallized lactitol monohydrate.

In particular it is very advantageous to mix 1 part by weight of a lactitol solution having a concentration of 70 percent by weight with 1 part by weight of ethanol at 60° C. and then to cool the mixture to 25° C. while agitating whereupon the lactitol monohydrate crystallizes.

A X-ray diffraction analysis has been performed on a single crystal of lactitol dihydrate in order to determine the crystal structure thereof. This analysis shows that the dihydrate crystal belongs to the tetragonal crystal system and that unit cell comprises 8 lactitol molecules and 16 water molecules. The second water molecule is lodged within the space between the sorbitol chain and the galactopyranosyl ring as will be apparent from the projection formula (FIG. 1). The dimensions of the unit cell are: a=b=8.762 Å, c=45.508 Å; hence this unit cell is indeed very elongated. The space group is $P4_32_12$, the cell volume is 3493.8 Å$^3$ and the calculated density of the crystal is 1.445 g/cm$^3$.

A single crystal of lactitol dihydrate is now prepared for the first time. The lactitol dihydrate known thus far was of insufficient purity for the preparation of a single crystal. Thereby is became now possible to perform a X-ray diffraction analysis (vide Table A).

TABLE A

| | Lactitol monohydrate | Lactitol dihydrate |
|---|---|---|
| Formula | $C_{12}H_{24}O_{11}\cdot H_2O$ | $C_{12}H_{24}O_{11}\cdot 2H_2O$ |
| Crystal system | orthorhombic | tetragonal |
| Dimensions of the unit cell | a = 7.808 (2) Å | a = b = 8.762 (2) Å |
| | b = 12.685 (2) Å | c = 45.508 (10) Å |
| | C = 15.931 (3) Å | |
| systematic extinctions | h00, h = 2n + 1 | h00, h = 2n + 1 |
| | 0k0, k = 2n + 1 | 0k0, k = 2n + 1 |
| | 001, l = 2n + 1 | 001, l = 4n + 1 |
| Space group | $P2_12_12_1$ | $P4_32_12$ |
| Number of molecules per unit cell | 4 | 8 |
| Unit cell volume | 1577.9 Å$^3$ | 3493.8 Å$^3$ |
| Density (calculated) | 1.523 g · cm$^{-3}$ | 1.445 g · cm$^{-3}$ |
| Number of reflections measured | 2081 | 2458 |
| Number of reflections observed | 1781 | 2091 |
| Number of parameters | 296 | 311 |
| Reliability index (full matrix least squares) | 0.032 | 0.041 |

Lactitol monohydrate

Apart from the dihydrate there has now been found also a new type of crystal containing only one molecule of crystal water, thus a monohydrate. It is true that in Agricultural and Food Chemistry Van Velthuysen describes a compound indicated to be lactitol monohydrate but it has appeared however at a later date that this product is impure and yet contains 1 percent by weight of lactulitol (4β-D-Galactosyl-D-mannitol) and 3% of mannitol en has a melting point of 94°–97° C., whereas the newly found product is pure and has a melting point of 121°–123° C. The solubility differs also. The solubility of the pure monohydrate in water at room temperature is less (56%) than that of the impure product (64%).

Lactitol monohydrate shows when heated at 130° C. for three days contrary to lactitol dihydrate a loss of weight of 2%.

It has now been found that pure lactitol monohydrate may be produced by crystallization of lactitol from an alcoholic medium.

It has also been found that lactitol monohydrate may be obtained by crystallization of an aqueous solution of lactitol at temperatures between 10° C. and 50° C. when the solution is seeded under proper conditions with crystalline lactitol monohydrate seeds obtained from an alcoholic medium.

Surprisingly it appears to be possible to obtain the monohydrate by a first crystallization whereupon lactitol dihydrate crystallizes from the mother liquor. Thus is illustrated in example XI.

A single crystal of lactitol monohydrate obtained from an ethanol-water medium has likewise been subjected to a X-ray diffraction analysis in order to determine the crystal structure thereof. From this analysis it has become apparent that the monohydrate crystal belongs to the rhombic crystal system and that the unit cell contains 4 lactitol molecules and 4 water molecules. The dimensions of the unit cell are: a=7.808 Å, b=12.685 Å and c=15.931 Å. The space group is $P2_12_12_1$, the unit cell volume is 1577.9 Å$^3$ and the calculated density of the crystal is 1.523 g/cm$^3$. The structure has been represented in FIG. 2 (vide also Table A). This structure likewise holds for lactitol monohydrate obtained by crystallization from an aqueous medium. The similarity between both forms of crystal is apparent from the fact that they yield identical powder diagrams and show a similar melting point behaviour when determined with the aid of differential-scanning calorimetry.

A melting point of 120°–123° C. for lactitol monohydrate determined with a melting point microscope corresponds to a melting point of 96.7°–102° C. when determined by Differential Scanning Calorimetry (DSC).

EXAMPLE 1

A lactitol solution purified by passing over ion exchangers and having a refractive index of 30° Brix was concentrated under reduced pressure to an index of 75° Brix (dry solids content of 71.6 percent by weight). From this lactitol sirope 2500 g were taken. Upon cooling to 18° C. crystals separated slowly from the syrup which crystals were removed from the mother liquor by centrifuging and then dried at 50° C.

Yield: 1190 g lactitol dihydrate or 60% based in 1791 g dry solids.

Melting point: 79°–80° C.; moisture content (Karl Fischer): 9.7 percent by weight. The mother liquor had a refractive index of 58° Brix (dry solids content of 55.4 percent by weight).

EXAMPLES II–V

The crystallization conditions are not limited to those mentioned in example I. It appears to be possible to recover crystalline lactitol dihydrate from lactitol solutions having different lactitol concentrations. In each instance an amount of 1600 g lactitol dihydrate was dissolved to that effect in 930 g, 730 g, 550 g and 400 g water, respectively. Upon cooling to 25° C. each one of the solutions was seeded with 16 g ground lactitol dihydrate followed by further cooling to 15° C. After 24 hours the crystals produced were separated from the mother liquor by centrifuging whereupon the crystals were washed with 50 ml water in the centrifuge and dried at a temperature of 50° C. In Tabel B the results thus obtained are summarized. The crystallization yields indicated in percent include the 1 percent by weight of crystal seeds.

From the results summarized in Tabel B is may be concluded that an increase of the initial lactitol concentration increases the crystallization yield at the same lactitol content in the mother liquor. At an initial concentration of less than 57 percent by weight of lactitol the crystallization yield will become less than 30% i.e. too low for the application on an industrial scale. At an initial concentration of more than 72 percent by weight a thick crystal slurry is formed which cannot be worked up anymore on an industrial scale.

TABLE B

| Example | lactitol dihydrate (g) | water (g) | lactitol product (% by wt) | lactitol product (g) | melting point (°C.) | water content (%) | mother liquor (g) | mother liquor (bx) | cryst yield (%) |
| --- | --- | --- | --- | --- | --- | --- | --- | --- | --- |
| I | 1600 | 930 | 57 | 480 | 80–81 | 10.9 | 1857 | 54 | 30.0 |
| III | 1600 | 730 | 62 | 776 | 80–81 | 10.8 | 1329 | 54 | 42.5 |
| IIV | 1600 | 550 | 67 | 987 | 80–81 | 10.7 | 945 | 54 | 61,7 |
| V | 1600 | 400 | 72 | 1040 | 78–80 | 10.7 | 821 | 55 | 65.0 |

EXAMPLE VI 225 g water was added to 760 lactitol dihydrate whereupon the mixture was heated to 100° C. while agitating whereby a clear 70 percent by weight lactitol solution was obtained. Upon cooling to 60° C. 1.3 l ethanol (96%) was added in small increments while agitating and keeping the temperature at 60° C. Upon cooling to 45° C. lactitol started to crystallize. After continued cooling to room temperature while agitating the product was recovered on a suction filter and dried at 50° C. in a drying cabinet. The yield of lactitol monohydrate was 684 g or 94% based on the lactitol used, melting point: 121°–123° C.; moisture content: 5.8 percent by weight (Karl Fischer).

EXAMPLES VII–X

Crystalline lactitol monohydrate was prepared from aqueous lactitol solutions having different lactitol contents varying from 70 to 80 percent by weight. Thereby in each instance an amount of 1700 g lactitol dihydrate was dissolved in 490 g, 350 g, 300 g and 230 g water, respectively, at a temperature of 100° C. Upon cooling to 50° C. the solution was seeded with 15 g ground lactitol monohydrate whereupon the cooling was continued to 45° C. After a crystallization for 24 hours at 45° C. the crystals were separated from the mother liquor in a laboratory centrifuge, washed with 50 ml water in the centrifuge and dried at 50° C. in a drying cabinet. Thereupon the mother liquors were also seeded with monohydrate crystals. After a crystallization for 24 hours at 15° C. the monohydrate crystals formed were separated by centrifuging, washed with 25 ml water and dried at 50° C. The results trhus obtained are compiled in Tabel C.

TABLE C

| Example | lactitol used (% by wt) | product (g) | melting point (°C.) | crystal water content (% by wt) | crystallization yield (%) | ibid total (°C.) | mother liquor (g) | mother liquor (bx) |
|---|---|---|---|---|---|---|---|---|
| VII | 70 | 310 | 115–120 | 5.3 | 19 | 59 | 1628 | 70.5 |
|  |  | 655 | 118–121 | 5.2 | 40 |  | 850 | 54 |
| VIII | 75 | 666 | 118–120 | 5.2 | 41 | 65 | 1101 | 71 |
|  |  | 395 | 123 | 5.1 | 24 |  | 608 | 54 |
| IX | 77 | 740 | 115–120 | 5.4 | 45 | 68 | 1059 | 71 |
|  |  | 372 | 123 | 5.3 | 23 |  | 598 | 54 |
| X | 80 | 912 | 110–120 | 5.4 | 56 | 77 | 844 | 71 |
|  |  | 341 | 123 | 5.6 | 21 |  | 341 | 54 |

From these tests it is apparent that an increase of the lactitol concentration from 70 percent by weight to 80 percent by weight causes the crystallization yield of the first crystallization to increase strongly whereas contrary thereto the yield of the second crystallization however decreases. The total crystallization yield however rises when increasing the lactitol concentration to almost 80%. From the mother liquors of the first crystallization pure monohydrate is crystallized again.

EXAMPLE XI 500 g water were added to 3800 g lactitol dihydrate and the mixture was heated to 100° C. whereby a clear 80 percent by weight lactitol solution was obtained. Upon cooling to 45° C. the solution was seeded with 36 g ground lactitol monohydrate resulting in the crystallization of the solution accompanied by generating of heat (a rise in temperature from 45° C. to 55° C. occurred).

After a crystallization for 24 hours at 45° C. the crystals were separated from the mother liquor in a laboratory centrifuge; after removal of the mother liquor by centrifuging the product was washed with 100 ml water in total in the centrifuge. The yield of the product dried at 50° C. was 2010 g lactitol monohydrate or 55% based on the lactitol used. The melting point of the product was 121°–123° C. and the moisture content was 5.2 percent by weight.

The mother liquor (1910 g of 76.5° Brix) was seeded with 15 g ground lactitol dihydrate and subsequently cooled to 15° C. After a crystallization for 24 hours at 15° C. the crystals were removed by centrifuging and washed with 40 ml water in the centrifuge.

The yield of lactitol dihydrate dried at 50° C. was 810 g or 21% based on the lactitol used. The melting point was 78°–79° C. and the moisture content was 9.7 percent by weight. Accordingly the total crystallization yield was 55%+21%=76%. The final mother liquor obtained to 1060 g of 59° C. Brix (dry solids content of 56 percent by weight).

EXAMPLES XII–XXVII

Examples XII–XXVII elucidate the conditions at which lactitol monohydrate and lactitol dihydrate, respectively, may be obtained from aqueous solutions of lactitol. In each instance 200 g lactitol dihydrate was used as the starting material which wasd dissolved in an amount of water varying from 40 g to 50 g at 100° C. Thereupon the solutions obtained were cooled to a temperature varying from 25° C. to 45° C. and seeded with 2 g monohydrate or 2 g dihydrate. The crystallization proper occurred at temperatures between 18° C. and 45° C.

The obtained crystals were separated from the mother liquor in a small model laboratory centrifuge, washed with 5 ml water in the centrifuge and dried at 50° C. The melting point of each fraction of crystalline lactitol was determined.

In Table D (examples XII to XXI, inclusive) the results are compiled which were obtained when the crystallization temperature was kept at the seeding temperature. It appears in general that upon seeding with monohydrate there is again formed the monohydrate whereas seeding with dihydrate yields again dihydrate. The test performed at 45° C. however is an exception in that solely the monohydrate was formed. At this temperature (and presumebly also at yet higher temperatures) the monohydrate is apparently the sole stable modification.

TABLE D

| Example | lactitol dihydrate (g) | water (g) | lactitol (% by wt) | seeding temp. (°C.) | seeds | produkt (g) | melting point (°C.) | crystals | Mother liquor (bx) |
|---|---|---|---|---|---|---|---|---|---|
| XII | 200 | 40 | 75.4 | 45 | mono | 77 | 121–123 | mono | 68 |
| XIII | 200 | 40 | 75.4 | 45 | di | 68 | 115–123 | mono | 68 |
| XIV | 200 | 45 | 73.9 | 37 | mono | 63 | 122–123 | mono | 67 |
| XV | 200 | 45 | 73.9 | 37 | di | 100 | 81–83 | di | 65 |
| XVI | 200 | 45 | 73.9 | 35 | mono | 76 | 122–124 | mono | 65 |
| XVII | 200 | 45 | 73.9 | 35 | di | 112 | 81–83 | di | 63 |
| XVIII | 200 | 45 | 73.9 | 32 | mono | 78 | 122–123 | mono | 59 |
| XIX | 200 | 45 | 73.9 | 32 | di | 106 | 81–83 | di | 61 |
| XX | 200 | 48 | 73.0 | 25 | mono | 88 | 121–123 | mono | 58 |
| XXI | 200 | 48 | 73.0 | 25 | di | 119 | 80–82 | di | 54 |

TABLE E

| Example | lactitol dihydrate (g) | water (g) | lactitol (% by wt) | seeding temp. (°C.) | seeds | cryst. temp. (°C.) | product (g) | melting point (°C.) | crystals | mother liquor (bx) |
|---------|------|----|------|----|------|----|-----|---------|------|----|
| XXII    | 200  | 42 | 74.8 | 45 | mono | 18 | 106 | 121–123 | mono | 58 |
| XXIII   | 200  | 42 | 74.8 | 45 | di   | 18 | 132 | 81–83   | di   | 54 |
| XXIV    | 200  | 50 | 72.4 | 37 | mono | 18 | 96  | 123–125 | mono | 54 |
| XXV     | 200  | 50 | 72.4 | 37 | di   | 18 | 126 | 80–82   | di   | 54 |
| XXVI    | 200  | 50 | 72.4 | 25 | mono | 18 | 99  | 122–124 | mono | 54 |
| XXVII   | 200  | 50 | 72,4 | 25 | di   | 18 | 124 | 81–83   | di   | 54 |

The results compiled in Table E (examples XXII to XXVII, inclusive) were obtained at one and the same crystallization temperature (18° C.) whereas the seeding temperature varied from 45° C. to 25° C. It appears that seeding with the monohydrate again yields the monohydrate and seeding with the dihydrate again yields the dihydrate. The difference in comparison with example XIII consists therein that if a seeding with the dihydrate performed at 45° C. is followed by a crystallization at 18° C. (example XXIII) there is now produced the dihydrate instead of the monohydrate like in example XIII. Due to the rapid cooling from 45° C. to 18° C. the seeding material did apparently not have the opportunity to convert from the dihydrate form to the monohydrate form.

A blended sample was made of all the monohydrate products obtained by the tests of examples XII to XXVII, inclusive, which sample was analyzed with respect to the moisture content in accordance with the Karl Fischer method; the moisture content was found to be 5.2 percent by weight. The blended sample of the dihydrates was found to have a moisture content of 10.0 percent by weight.

EXAMPLE XXVIII 950 g lactitol dihydrate (860 g anhydric lactitol) were dissolved in 125 g water at 100° C. Upon cooling to 50° C. the 80 percent by weight lactitol solution was seeded with 9.5 g ground dihydrate (1 percent by weight based on the lactitol dissolves). After crystallization for 48 hours at 45° C. the crystals formed were separated from the mother liqouor in a laboratory centrifuge, washed with 25 ml water and dried at 45° C. (drying cabinet). There were then obtained 440 g lactitol monohydrate (melting point: 118°–120° C.; moisture content: 4.9%) or 49% based on the lactitol used.

After a crystallization for 24 hours at 15° C. there could be recovered from the mother liquor seeded with 4 g ground dihydrate a further crop of 240 g lactitol dihydrate (melting: 80°–82° C.; moisture content: 10.0%) or 25% based on the lactitol used.

The total crystallization yield thus amounted to 49%+25%=74%.

EXAMPLE XXIX

This example illustrates the direct production of lactitol monohydrate from a purified and concentrated hydrogenated lactose solution.

2500 g purified concentrated lactitol syrup (80° Brix, 76.4 percent by weight of dry solids) were seeded with 15 g ground lactitol monohydrate at 45° C. After a crystallization for 48 hours at 45° C. the crystals were separated from the mother liquor in a laboratory centrifuge, washed with 50 ml water and dried at 45° C. (drying cabinet). Yield: 875 g monohydrate or 43.5 percent by weight based on the dry solids content of the lactitol syrup; melting point 110°–120° C.; moisture content: 5.7 percent by weight.

Upon seeding with about 5 g ground monohydrate there was yet crystallized from the mother liquor a further crop 446 g lactitol monohydrate or 22.2 percent by weight based on the dry solids content; melting point: 115°–120° C.; moisture content: 5.5 percent by weight.

After about 1 week at 18°–20° C. there was crystallized from the second mother liquor yet 202 g lactitol dihydrate of 9.6 percent by weight based on the dry solid content; melting point: 82°–84° C.; moisture content: 9.8 percent by weight.

The total crystallization yield thus amounted to 75.3% including 1% of seeding crystals.

The final mother liquor yet showed a refractive index of 57° Brix (dry solids content of 54 percent by weight).

EXAMPLE XXX

The hydrogenated lactose solution described in example XXIX was used as the starting material. This solution was concentrated to 75° Brix (dry solids content of 72 percent by weight). The solution was seeded with lactitol dihydrate at room temperature. Hereby only the lactitol dihydrate crystallized. The crystallization yield was 60%.

We claim:

1. A method for the production of crystalline lactitol monohydrate having a melting point of 110°–125° C. determined with a melting point microscope and having lattice cell constants a=7.808(2) Å, b=12.685(2) Å and c=15.931(3) Å with a structure as represented in FIG. 2, said method consisting essentially of the steps of seeding a solution of from 70 to 85 percent by weight of lactitol in water as the sole solvent with a hydrate of lactitol selected from the group consisting of lactitol monohydrate and lactitol dihydrate at from 45° C. to 55° C. and causing the lactitol monohydrate to crystallize at 45° C.

2. The method of claim 1, wherein the water solution contains from 78 to 82 percent by weight of lactitol.

3. The method of claim 2, further comprising the steps of separating crystallized lactitol monohydrate and a mother liquor and recovering the crystallized lactitol monohydrate.

4. The method of claim 3, further comprising the steps of seeding the mother liquor with lactitol monohydrate at from 15° C. to 25° C. and causing a second batch of lactitol monohydrate to crystallize at from 15° C. to 25° C.

5. The method of claim 4, wherein the mother liquor is cooled to from 18° C. to 22° C. prior to seeding.

6. The method of claim 4, wherein lactitol monohydrate is caused to crystallize at from 18° C. to 22° C.

7. A method for the production of crystalline lactitol hydrates consisting essentially of the steps of seeding a solution of from 70 to 85 percent by weight of lactitol in water as the sole solvent with a lactitol hydrate selected from the group consisting of lactitol monohydrate and lactitol dihydrate at from 45° C. to 55° C., causing a first batch of lactitol monohydrate having a melting point of 110°–125° C. determined with a melting point microscope and having lattice cell constants a=7.808(2) A, b=12.685(2) A and c=15.931(3) A with a structure as represented in FIG. 2 to crystallize at 45° C., separating the first batch of crystallized lactitol monohydrate from the solution to form a first mother liquor, cooling the first mother liquor to from 15° C. to 25° C., seeding the first mother liquor with crystalline lactitol monohydrate, causing a second batch of lactitol monohydrate to crystallize at from 15° C. to 25° C., separating the second batch of crystallized lactitol monohydrate to form a second mother liquor, causing the second mother liquor to crystallize at from 10° C. to 25° C. to form lactitol dihydrate having a melting point of 78°–83° C. determined with a melting point microscope and lattice cell constants a=b= 8.762(2) Å and c=45.508(10) Å with a structure as represented in FIG. 1 and recovering the crystallized lactitol dihydrate.

8. The method of claim 7, wherein lactitol dihydrate is caused to crystallize at from 15° C. to 20° C.

* * * * *